United States Patent
Li et al.

(10) Patent No.: US 11,000,234 B2
(45) Date of Patent: May 11, 2021

(54) WEARABLE DEVICE, METHOD AND APPARATUS FOR ELIMINATING MOTION INTERFERENCE

(71) Applicant: SHENZHEN GOODIX TECHOLOGY CO., LTD., Guangdong (CN)

(72) Inventors: Guoliang Li, Guangdong (CN); Xinshan Wang, Guangdong (CN); Ke Yang, Guangdong (CN); Duan Zeng, Guangdong (CN); Fahai Chen, Guangdong (CN)

(73) Assignee: SHENZHEN GOODIX TECHNOLOGY CO., LTD., Shenzhen (CN)

( * ) Notice: Subject to any disclaimer, the term of this patent is extended or adjusted under 35 U.S.C. 154(b) by 278 days.

(21) Appl. No.: 16/049,075

(22) Filed: Jul. 30, 2018

(65) Prior Publication Data

US 2018/0338728 A1 Nov. 29, 2018

Related U.S. Application Data

(63) Continuation of application No. PCT/CN2017/083846, filed on May 10, 2017.

(51) Int. Cl.
*A61B 5/00* (2006.01)
*A61B 5/024* (2006.01)

(52) U.S. Cl.
CPC .......... *A61B 5/721* (2013.01); *A61B 5/02416* (2013.01); *A61B 5/02438* (2013.01);
(Continued)

(58) Field of Classification Search
CPC . A61B 5/572; A61B 5/02416; A61B 5/02438; A61B 5/7225; A61B 5/7246; A61B 5/721
See application file for complete search history.

(56) References Cited

U.S. PATENT DOCUMENTS

2010/0145171 A1 6/2010 Park et al.
2015/0196257 A1 7/2015 Yousefi et al.
(Continued)

FOREIGN PATENT DOCUMENTS

CN 101082504 A 12/2007
CN 105184325 A 12/2015
(Continued)

OTHER PUBLICATIONS

Chinese Office Action for Chinese Application No. 201780000400.4 dated Sep. 19, 2019.
(Continued)

*Primary Examiner* — Bryan Bui
(74) *Attorney, Agent, or Firm* — Heslin Rothenberg Farley & Mesiti P.C.

(57) ABSTRACT

A method for eliminating motion interference includes: performing dimensionality reduction on the multi-dimensional acceleration signal to obtain a one-dimensional acceleration signal that represents motion interference; mixing the first signal and the second signal through a plurality of preset coefficients $r_i$ respectively, so as to calculate a plurality of mixed signals corresponding to the plurality of preset coefficients; calculating a correlation coefficient between each of the mixed signals and the one-dimensional acceleration signal; obtaining a preset coefficient corresponding to the maximum correlation coefficient among the correlation coefficients and a preset coefficient corresponding to the minimum correlation coefficient among the correlation coefficients; and calculating a signal with motion interference being eliminated from the measurement signal to be processed, according to the first signal, the second signal, the preset coefficient corresponding to the maximum correlation coefficient, and the preset coefficient corresponding to the minimum correlation coefficient.

10 Claims, 4 Drawing Sheets

(52) U.S. Cl.
   CPC .......... *A61B 5/7225* (2013.01); *A61B 5/7246* (2013.01); *A61B 2562/0219* (2013.01)

(56) References Cited

U.S. PATENT DOCUMENTS

| | | |
|---|---|---|
| 2016/0038045 A1 | 2/2016 | Shapiro |
| 2016/0120477 A1 | 5/2016 | Takahashi |
| 2016/0235374 A1* | 8/2016 | Miller ................ A61B 5/02055 |
| 2016/0302674 A1 | 10/2016 | Moyer et al. |
| 2018/0085040 A1* | 3/2018 | Ferber ................ A61B 5/0816 |

FOREIGN PATENT DOCUMENTS

| | | |
|---|---|---|
| CN | 105249940 A | 1/2016 |
| CN | 105832315 A | 8/2016 |
| CN | 105919584 A | 9/2016 |
| WO | 2017063086 A1 | 4/2017 |

OTHER PUBLICATIONS

International Search Report (and English translation) and Written Opinion of the International Searching Authority for International Application No. PCT/CN2017/083846 dated Feb. 14, 2018.
Extended European Search Report for European Patent Application No. 17893507.8 dated Mar. 18, 2021.

* cited by examiner

FIG. 6 he present disclosure is a continuation of international application No. PCT/CN2017/083846, filed on May 10, 2017, which is hereby incorporated by reference in its entirety.

WEARABLE DEVICE, METHOD AND APPARATUS FOR ELIMINATING MOTION INTERFERENCE

CROSS-REFERENCE TO RELATED APPLICATIONS

The present disclosure is a continuation of international application No. PCT/CN2017/083846, filed on May 10, 2017, which is hereby incorporated by reference in its entirety.

TECHNICAL FIELD

The present disclosure relates to the field of signal processing technology, and more particularly to a wearable device, a method and apparatus for eliminating motion interference.

BACKGROUND

With the improvement of living standards, people pay more and more attention to their own health. Heart rate is the speed of the heartbeat measured by the number of contractions of the heart per minute, and it is a very important physiological indicator in clinical diagnosis. Traditional medical devices require users to be at rest while measuring heart rate, and are not convenient to be carried. Therefore, many manufacturers have already produced wearable devices capable of performing heart rate measurement, so that users can measure heart rate in daily life occasions.

The existing most commonly used method for measuring heart rate is Photoplethysmogram (PPG) method. In this method, a LED is used to emit light of a specific wavelength, the light is propagated, scattered, diffracted, and reflected via human tissue, then returned, and a returned optical signal is converted into an electrical signal, so as to obtain a corresponding PPG signal. When light beams are propagated through human tissues, intensity of light beams is attenuated due to the property of light absorbing by human tissues. For example, a value of light absorbing by static tissues such as skin, fat, muscle, etc. is a constant value. However, light absorbing by blood undergoes periodic volume changes due to contraction and diastole of the heart, thus the PPG signal shows a periodic waveform that is consistent with the heartbeat. Accordingly, the heartbeat frequency can be measured with the PPG signal. Further, the PPG method is a non-invasive measurement method for measuring heart rate.

The inventor has found that there are at least the following problems: heart rate measurement on the wearable device is more demanding on the PPG method because users need to measure the heart rate in a motion state. However, muscle and pressure will change in a motion state, which results in that a propagation path of light beams changes. Besides a pulse wave signal, a motion interference signal is also superimposed on the PPG signal. Different motion states produce different motion interference frequencies, and a value of the motion frequency cannot be guaranteed to be a constant value. For example, the motion frequency is in a range of 0 Hz to 4 Hz in the state of walking, climbing and running, and the human heart rate is also in a range of 0.5 Hz to 4 Hz. Therefore, motion interference with unknown frequencies cannot be filtered by traditional FIR (finite impulse response), IIR (infinite impulse response) or wavelet filtering.

There are two existing technical solutions for measuring heart rate in a motion state: one is an adaptive noise cancellation method based on an adaptive filter; and the other is an oxygen saturation discrete saturation transform (DST) method. However, a precondition for implementing the adaptive noise cancellation method is that the motion state has statistical stability, in this way, the adaptive filter is continuously in a convergent state. But the motion state cannot be kept stable in reality, such as up and down stairs. A precondition for the DST method is that blood oxygen saturation is relatively high, usually higher than 85%, thus this method is not suitable for users with dyspnea (whose blood oxygen saturation is relatively low). In addition, the DST method is computationally intensive and difficult to be implemented on wearable devices.

SUMMARY

The objective of some embodiments of the present disclosure is to provide a wearable device, a method and apparatus for eliminating motion interference, with which interference in motion can be effectively eliminated, and detection of signals with motion interference being eliminated is suitable in various motion states, meanwhile computational complexity is less, and implementation is easily performed on the wearable device.

An embodiment of the present disclosure provides a method for eliminating motion interference. The method is applied to a wearable device capable of acquiring a multi-dimensional acceleration signal and a measurement signal to be processed of the wearable device, and the measurement signal to be processed includes a first signal and a second signal having different wavelengths. The method comprises: performing dimensionality reduction on the multi-dimensional acceleration signal to obtain a one-dimensional acceleration signal that represents motion interference; mixing the first signal and the second signal through a plurality of preset coefficients respectively, so as to calculate a plurality of mixed signals corresponding to the plurality of preset coefficients; calculating a correlation coefficient between each of the mixed signals and the one-dimensional acceleration signal; obtaining a preset coefficient corresponding to the maximum correlation coefficient among the correlation coefficients and a preset coefficient corresponding to the minimum correlation coefficient among the correlation coefficients; calculating a signal with motion interference being eliminated from the measurement signal to be processed, according to the first signal, the second signal, the preset coefficient corresponding to the maximum correlation coefficient, and the preset coefficient corresponding to the minimum correlation coefficient.

An embodiment of the present disclosure further provides an apparatus for eliminating motion interference. The apparatus is applied to the method for eliminating motion interference as described above. The apparatus comprises: a dimensionality reduction module configured to perform dimensionality reduction on a multi-dimensional acceleration signal to obtain a one-dimensional acceleration signal that represents motion interference; a first calculation module configured to mix a first signal and a second signal through a plurality of preset coefficients respectively, so as to calculate a plurality of mixed signals corresponding to the plurality of preset coefficients; a second calculation module configured to calculate a correlation coefficient between each of the mixed signals and the one-dimensional acceleration signal; an identification module configured to obtain a preset coefficient corresponding to the maximum correlation coefficient among the correlation coefficients and a preset coefficient corresponding to the minimum correlation coefficient among the correlation coefficients; and a third calculation module configured to calculate a signal with motion interference being eliminated from the measurement signal to be processed, according to the first signal, the second signal, the preset coefficient corresponding to the maximum correlation coefficient, and the preset coefficient corresponding to the minimum correlation coefficient.

An embodiment of the present disclosure further provides a wearable device. The wearable device comprises a first sensor, a second sensor, a memory, and a processor connected to the first sensor and the second sensor. The first sensor is configured to acquire a multi-dimensional acceleration signal of the wearable device. The second sensor is configured to obtain a measurement signal to be processed, and the measurement signal to be processed includes a first signal and a second signal having different wavelengths. The memory is configured to store a plurality of instructions. The processor is configured to load the plurality of instructions and perform the function of the apparatus for eliminating motion interference as described above.

In the embodiments of the present disclosure, dimensionality reduction is performed on the multi-dimensional acceleration signal to obtain a one-dimensional acceleration signal that represents motion interference; the first signal and the second signal are mixed through a plurality of preset coefficients respectively, and a plurality of mixed signals corresponding to the plurality of preset coefficients are calculated; a correlation coefficient between each of the mixed signals and the one-dimensional acceleration signal is calculated accordingly; then a preset coefficient corresponding to the maximum correlation coefficient among the correlation coefficients and a preset coefficient corresponding to the minimum correlation coefficient among the correlation coefficients are obtained; so that a signal with motion interference being eliminated from the measurement signal to be processed is calculated according to the first signal, the second signal, the preset coefficient corresponding to the maximum correlation coefficient, and the preset coefficient corresponding to the minimum correlation coefficient. That is, interference in motion is eliminated by using the correlation between motion interference and the multi-dimensional acceleration signal, and detection of signals with motion interference being eliminated is suitable in various motion states, meanwhile computational complexity is less, and implementation is easily be performed on the wearable device.

Further, in the method for eliminating motion interference, the mixed signal $D_{r_i}(t)$ is: $D_{r_i}(t)=S_{\lambda_a}(t)-r_i \cdot S_{\lambda_b}$, $i=1, 2, 3, \ldots$; $S_{\lambda_a}(t)$ represents the first signal; $S_{\lambda_b}$ represents the second signal; $r_i$ represents an i-th preset coefficient, and a traversal range of $r_i$ is $[r_{slow}, r_{high}]$, $r_{slow}$, $r_{high}$ are a lower limit and an upper limit of the traversal range, respectively. This embodiment provides a specific method for calculating the mixed signal $D_{r_i}(t)$.

Further, in the method for eliminating motion interference, the signal with motion interference being eliminated is expressed as:

$$ppg_{\lambda_a}(t) = \frac{r_a(S_{\lambda_a}(t) - r_v \cdot S_{\lambda_b})}{(r_a - r_v)}, \text{ or } ppg_{\lambda_b}(t) = \frac{S_{\lambda_a}(t) - r_v \cdot S_{\lambda_b}}{(r_a - r_v)},$$

in which $g_{\lambda_a}(t)=r_a \cdot ppg_{\lambda_b}(t)$, and $ppg_{\lambda_a}(t)$ and $ppg_{\lambda_b}(t)$ represents the signal with motion interference being eliminated; $r_a$ represents the preset coefficient corresponding to the maximum correlation coefficient, $r_v$ represents the preset coefficient corresponding to the minimum correlation coefficient. This embodiment provides a specific formula for calculating the signal with motion interference being eliminated.

Further, in the method for eliminating motion interference, the correlation coefficient is a Pearson correlation coefficient. This embodiment provides a method for calculating the correlation coefficient.

Further, in the method for eliminating motion interference, performing dimensionality reduction on the multi-dimensional acceleration signal to obtain a one-dimensional acceleration signal that represents motion interference specifically comprises: calculating a covariance matrix of a multi-dimensional acceleration matrix formed by the multi-dimensional acceleration signal; calculating a plurality of eigenvalues and a plurality of eigenvectors of the covariance matrix, the plurality of eigenvalues corresponding to the plurality of eigenvectors respectively; identifying, according to the plurality of eigenvalues, an eigenvector that includes a preset information weight from the plurality of eigenvectors; and multiplying the eigenvector with the multi-dimensional acceleration signal to obtain the one-dimensional acceleration signal. This embodiment provides a specific method of implementing dimensionality reduction processing on the multi-dimensional acceleration signal.

Further, in the method for eliminating motion interference, the value of the plurality of preset coefficients is increased in an arithmetic progression manner.

Further, in the method for eliminating motion interference, the signal with motion interference being eliminated is a PPG signal.

Further, in the wearable device, the second sensor is a heart rate sensor.

BRIEF DESCRIPTION OF THE DRAWINGS

One or more embodiments are exemplified by the corresponding figures in the accompanying drawings, these illustrative explanations are not intended to limit these embodiments, elements with the same reference numbers in the drawings indicate similar elements. The figures in the accompany drawings do not present a proportional limit unless specifically declared.

DETAILED DESCRIPTION

In order to make a purpose, a technical solution, and advantages of the present disclosure clearer, some embodiments of the present disclosure will be described in detail in accordance with the accompanying drawings. It should be understood that, the specific embodiments described herein are only used to explain the present disclosure, rather than to limit the present disclosure.

A first embodiment of the present disclosure provides a method for eliminating motion interference. The method is applied to a wearable device, such as a watch, a ring, a headband, an earphone, etc. The wearable device can acquire a multi-dimensional acceleration signal and a measurement signal to be processed of the wearable device. The multi-dimensional acceleration signal represents an acceleration signal in different directions (that is, different dimensions) generated in motion state of the wearable device.

A light-emitting diode in the wearable device emits light of two different wavelengths, and an optical sensor capable of collecting optical signals of different wavelengths is disposed in the wearable device, therefore measurement signals to be processed that includes a first signal and a second signal having different wavelengths can be obtained. A signal with motion interference being eliminated can be obtained after eliminating motion interference in the measurement signal to be processed. Frequencies of the signals with motion interference being eliminated that are obtained from the first signal or the second signal are the same, that is, the wavelengths are the same. The signal with motion interference being eliminated is, for example, a PPG signal, and the measurement signal to be processed is actually a PPG signal including motion interference, thus the signal with motion interference being eliminated is obtained after motion interference in the measurement signal to be processed is eliminated.

Figure 1:
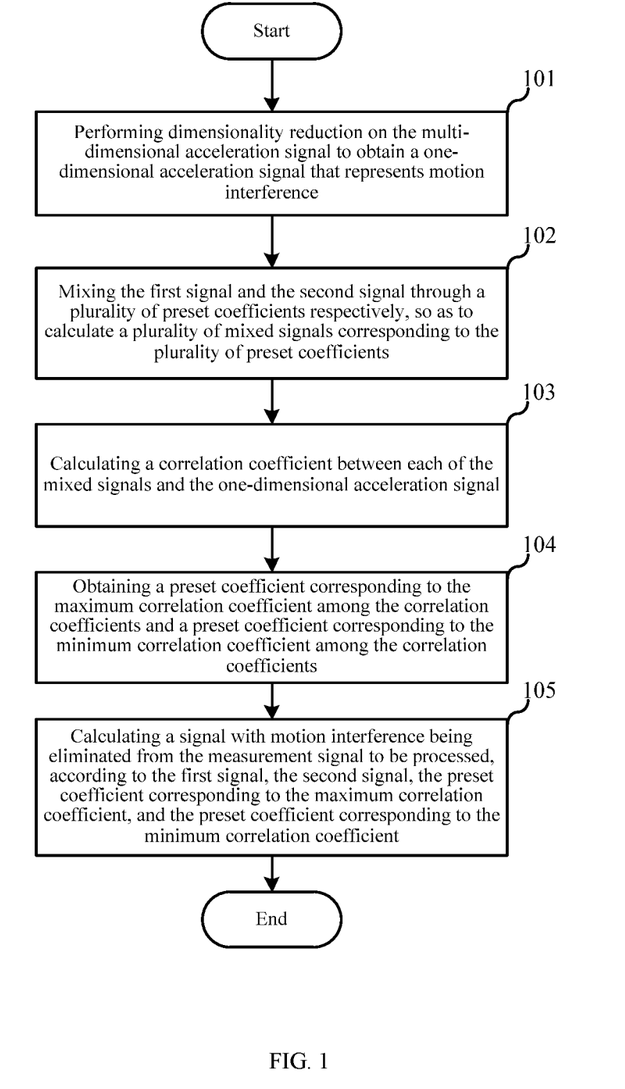
FIG. 1 is a detailed flowchart of a method for eliminating motion interference according to a first embodiment of the present disclosure.

This embodiment takes the measurement signal to be processed that is a PPG signal with motion interference as an example. The detailed process of the method for eliminating motion interference is shown in FIG. 1.

Step 101, dimensionality reduction is performed on the multi-dimensional acceleration signal to obtain a one-dimensional acceleration signal that represents motion interference.

Specifically, a multi-dimensional acceleration signal of a wearable device usually is a three-axis acceleration signal G(t), that includes acceleration signals in three directions of X-axis, Y-axis, and Z-axis (X-axis, Y-axis, and Z-axis are a coordinate system determined by a current direction of the wearable device). Dimensionality reduction processing is performed on the three-axis acceleration signal G(t), so that a one-dimensional acceleration signal Acc(t) can be extracted from the three-axis acceleration signal G(t). There is a strong correlation between the one-dimensional acceleration signal Acc(t) and a motion interference component in the measurement signal to be processed and there is no correlation between the one-dimensional acceleration signal Acc(t) and a pulse signal component in the measurement signal to be processed, thus the one-dimensional acceleration signal Acc(t) can be used to represent the motion interference.

Step 102, the first signal and the second signal are mixed through a plurality of preset coefficients respectively, so as to calculate a plurality of mixed signals corresponding to the plurality of preset coefficients.

Specifically, the first signal is a photoelectric signal $S_{\lambda_a}(t)$ with a wavelength of $\lambda_a$, the second signal is a photoelectric signal $S_{\lambda_b}(t)$ with a wavelength of $\lambda_b$. t is a time window with a length of T, $t=[t_0, t_0+T]$, the first signal $S_{\lambda_a}(t)$ and the second signal $S_{\lambda_b}(t)$ satisfy the following expressions:

$$S_{\lambda_a}(t)=ppg_{\lambda_a}(t)+M_{\lambda_a}(t)+N_{\lambda_a}(t)$$

$$S_{\lambda_b}(t)=ppg_{\lambda_b}(t)+M_{\lambda_b}(t)+N_{\lambda_b}(t)$$

Herein, $ppg_{\lambda_a}(t)$ and $ppg_{\lambda_b}(t)$ are pulse signal components (that is, the signal with motion interference being eliminated) in the first signal and the second signal, respectively. $M_{\lambda_a}(t)$ and $M_{\lambda_b}(t)$ are motion interference components in the first signal and the second signal, respectively. $N_{\lambda_a}(t)$ and $N_{\lambda_b}(t)$ are noise components in the first signal and the second signal, respectively. The pulse signal component, the motion interference component, and the noise component in each of the first signal and the second signal are independent of each other.

Figure 2:
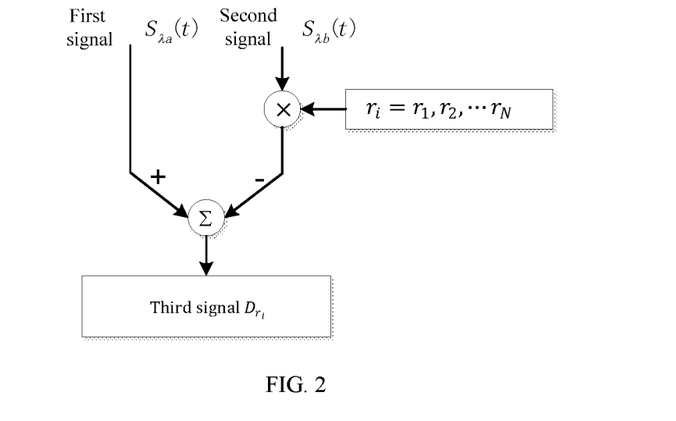
FIG. 2 is a schematic diagram of calculating a mixed signal according to the first embodiment of the present disclosure.

The first signal and the second signal are mixed through a preset coefficient $r_i$, as shown in FIG. 2, so that a mixed signal $D_{r_i}(t)$ can be obtained. The mixed signal $D_{r_i}(t)$ may be represented as:

$$D_{r_i}(t)=S_{\lambda_a}(t)-r_i \cdot S_{\lambda_b}, i=1, 2, 3, \ldots ;$$

Herein, $r_i$ represents an i-th preset coefficient, and a traversal range of $r_i$ is $[r_{slow}, r_{high}]$, $r_{slow}$ and $r_{high}$ are a lower limit and an upper limit of the traversal range, respectively. Preferably, the value of the plurality of preset coefficients $r_i$ is increased in an arithmetic progression manner.

It needs to be noted that, FIG. 2 merely schematically provides a method for calculating the mixed signal, this embodiment makes no limitations thereto, and specific setting may be made according to a practical design scheme.

The pulse signal component and the motion interference component in the first signal are correlated to the pulse signal component and the motion interference component in the second signal, respectively, so that the following expressions are satisfied:

$$ppg_{\lambda_a}(t)=r_a \cdot ppg_{\lambda_b}(t)$$

$$M_{\lambda_a}(t)=r_v \cdot M_{\lambda_b}(t)$$

Herein, the mixed signal $D_{r_i}(t)$ is correlated to the one-dimensional acceleration signal Acc(t), and there is a correlation coefficient. $r_a$ represents an a-th preset coefficient, that is the preset coefficient corresponding to the correlation coefficient that takes a maximum. $r_v$ represents a v-th preset coefficient, that is the preset coefficient corresponding to the correlation coefficient that takes a minimum. $r_a \neq r_v$.

In view of the above, the mixed signal $D_{r_i}(t)$ may be further represented as:

$$D_{r_i}(t) = S_{\lambda_a}(t) - r_i \cdot S_{\lambda_b}$$
$$= (r_a - r_i) \cdot ppg_{\lambda_b}(t) + (r_v - r_i) \cdot M_{\lambda_b}(t) + N(t)$$

Herein, $N(t)=N_{\lambda_a}(t)-r_i N_{\lambda_b}(t)$, it is the noise component, and it is uncorrelated to $ppg_{\lambda_b}(t)$ and $M_{\lambda_b}(t)$.

According to the above expression of the mixed signal $D_{r_i}(t)$, the plurality of preset coefficients $r_i$ are traversed within the traversal range $[r_{slow}, r_{high}]$, so as to calculate a plurality of mixed signals $D_{r_i}(t)$ corresponding to the plurality of preset coefficients. That is, each preset coefficient $r_i$ corresponds to one mixed signal $D_{r_i}(t)$.

Step 103, a correlation coefficient between each mixed signal and the one-dimensional acceleration signal is calculated.

Specifically, the existing correlation coefficient calculation methods include the Pearson correlation coefficient calculation method and the cosine similarity calculation method. This embodiment adopts the Pearson correlation coefficient calculation method, the correlation coefficient is a Pearson correlation coefficient. The Pearson correlation coefficient is irrelevant to amplitudes and baselines of the mixed signal $D_{r_i}(t)$ and the one-dimensional acceleration signal, and is only related to shapes of the mixed signal $D_{r_i}(t)$ and the one-dimensional acceleration signal, thus a shape similarity of the mixed signal $D_{r_i}(t)$ and the one-dimensional acceleration signal can be measured accurately.

The Pearson correlation coefficient calculation method calculates a Pearson correlation coefficient (that is, correlation coefficient) $\rho_{ri}$ of each mixed signal $D_{r_i}(t)$ and the one-dimensional acceleration signal $Acc(t)$:

$$\rho_{r_i} = \left| \frac{\text{cov}(D_{r_i}, Acc)}{\sigma_{D_{r_i}} \sigma_{Acc}} \right|$$

$$= \left| \frac{E\left( (D_{r_i} - \mu_{D_{r_i}}) \cdot (Acc - \mu_{Acc}) \right)}{\sigma_D \sigma_A} \right|$$

$$= \frac{|E(D_{r_i} \cdot Acc) - E(D_{r_i}) \cdot E(Acc)|}{\sqrt{E(D_{r_i}^2) - E^2(D_{r_i})} \cdot \sqrt{E(Acc^2) - E^2(Acc)}}$$

Herein, $\rho_{ri}$ represents a Pearson correlation coefficient of the mixed signal $D_{r_i}(t)$ corresponding to the i-th preset coefficient and the one-dimensional acceleration signal $Acc(t)$. Since each mixed signal $D_{r_i}(t)$ has one Pearson correlation coefficient (that is, correlation coefficient) $\rho_{ri}$, and each mixed signal $D_{r_i}(t)$ corresponds to one preset coefficient $r_i$, each Pearson correlation coefficient $\rho_{ri}$ corresponds to one preset coefficient $r_i$.

Figure 3:
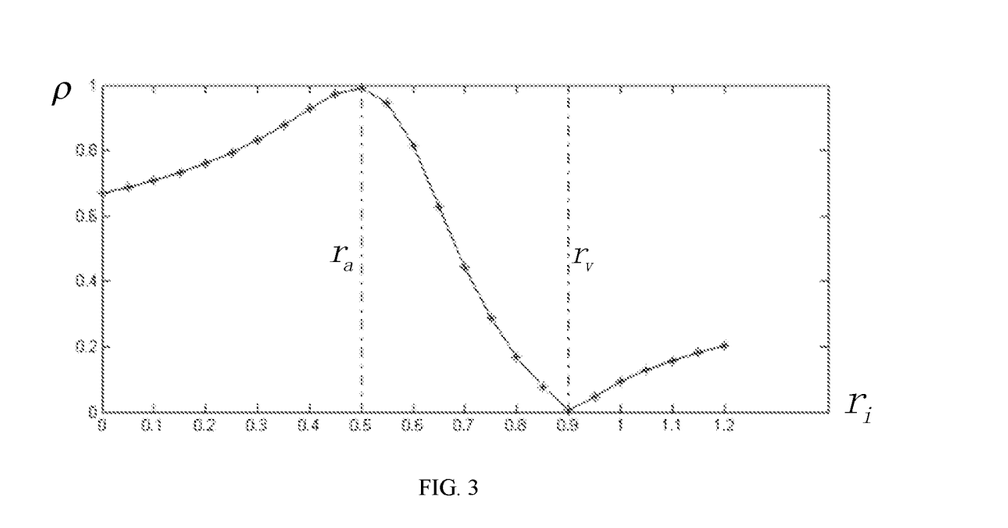
FIG. 3 is a curve diagram of a correlation coefficient and a preset coefficient according to the first embodiment of the present disclosure.
Figure 4:
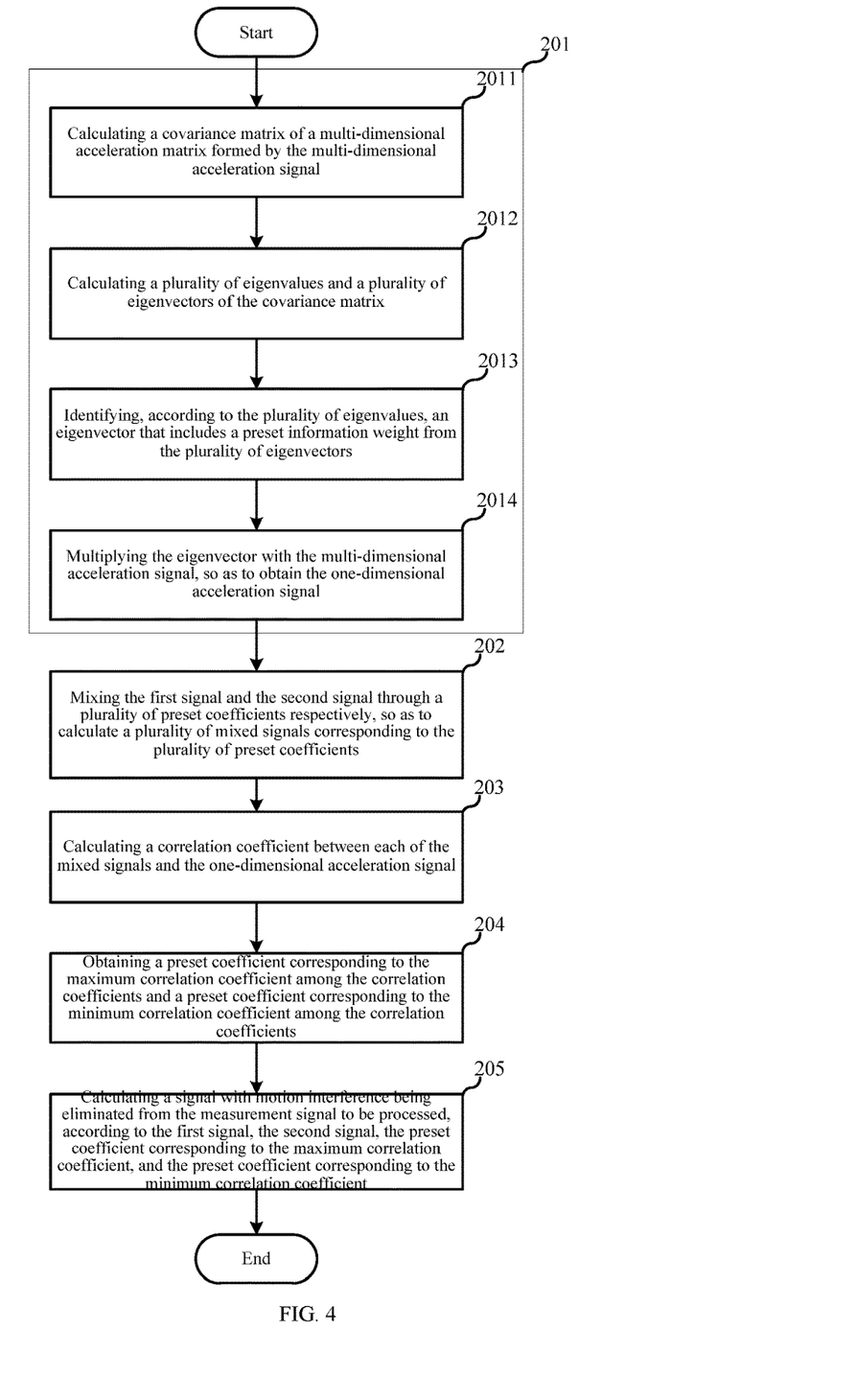
FIG. 4 is a detailed flowchart of a method for eliminating motion interference according to a second embodiment of the present disclosure.

In this embodiment, Pearson correlation coefficients (that is, correlation coefficients) $\rho_{ri}$ of i mixed signals $D_{r_i}(t)$ and the one-dimensional acceleration signal $Acc(t)$ are calculated respectively, that is, the i mixed signals $D_{r_i}(t)$ are sequentially substituted into the above Pearson correlation coefficient (that is, correlation coefficient) calculation formula, then i Pearson correlation coefficients (that is, correlation coefficients) $\rho_{ri}$ can be obtained. Referring to FIG. 3, a curve of the correlation coefficient $\rho_{ri}$ and the preset coefficient $r_i$ is shown.

Step 104, a preset coefficient corresponding to the maximum correlation coefficient among the correlation coefficients and a preset coefficient corresponding to the minimum correlation coefficient among the correlation coefficients are obtained.

Specifically, the maximum correlation coefficient and the minimum correlation coefficient are identified from among the plurality of correlation coefficients $\rho_{ri}$, and it can be known from the curve of the correlation coefficient $\rho_{ri}$ and the preset coefficient $r_i$ in FIG. 3, the maximum correlation coefficient is close to 1, and the minimum correlation coefficient is close to 0.

In addition, the mixed signal $D_{r_i}(t)=(r_a-r_i)\cdot ppg_{\lambda_b}(t)+(r_v-r_i)\cdot M_{\lambda_b}(t)+N(t)$, from which the following can be known:

When $r_i=r_a$, the mixed signal $D_{r_i}(t)=(r_v-r_a)\cdot M_{\lambda_b}(t)+N(t)$. In this case, the mixed signal $D_{r_i}(t)$ and the one-dimensional acceleration signal $Acc(t)$ have a strong correlation, and the correlation coefficient $\rho_{ri}$ takes a maximum value which is close to 1;

When $r_i=r_v$, the mixed signal $D_{r_i}(t)=(r_a-r_v)\cdot ppg_{\lambda_b}(t)+N(t)$. In this case, the mixed signal $D_{r_i}(t)$ and the one-dimensional acceleration signal $Acc(t)$ have a weak correlation, and the correlation coefficient $\rho_{ri}$ takes a minimum value which is close to 0.

Therefore, when the correlation coefficient $\rho_{ri}$ takes a maximum value which is close to 1, the correlation coefficient is $r_a$, and when the correlation coefficient $\rho_{ri}$ takes a minimum value which is close to 0, the correlation coefficient is $r_v$; that is, as shown in FIG. 3, the preset coefficient corresponding to the maximum correlation coefficient is $r_a$, which is 0.5, and a preset coefficient corresponding to the minimum correlation coefficient is $r_v$, which is 0.9.

Step 105, a signal with motion interference being eliminated from the measurement signal to be processed is calculated according to the first signal, the second signal, the preset coefficient corresponding to the maximum correlation coefficient, and the preset coefficient corresponding to the minimum correlation coefficient.

Specifically, when $r_i=r_v$, the mixed signal $D_{r_i}(t)$ and the one-dimensional acceleration signal $Acc(t)$ have a weak correlation. In this case, the mixed signal $D_{r_i}(t)$ is:

$$D_{rv}(t)=S_{\lambda_a}(t)-r_v\cdot S_{\lambda_b}=(r_a-r_v)\cdot ppg_{\lambda_b}(t)+N(t)$$

The $D_{rv}(t)$ signal only includes the pulse signal (that is, the signal with motion interface being eliminated) and other small amount of noise, and the motion interference component has been eliminated. However, the noise signal is small and negligible, so:

$$D_{rv}(t)=S_{\lambda_a}(t)-r_v\cdot S_{\lambda_b}=(r_a-r_v)\cdot ppg_{\lambda_b}(t)$$

Accordingly, the signal $ppg_{\lambda_b}(t)$ with motion interference being eliminated from the measurement signal to be processed can be calculated as:

$$ppg_{\lambda_b}(t) = \frac{S_{\lambda_a}(t) - r_v \cdot S_{\lambda_b}}{(r_a - r_v)}$$

Herein, $ppg_{\lambda_b}(t)$ represents the signal with motion interference being eliminated, $r_a$ represents the preset coefficient corresponding to the maximum correlation coefficient, $r_v$ represents the preset coefficient corresponding to the minimum correlation coefficient.

Accordingly, the signal with motion interference being eliminated may be represented by $ppg_{\lambda_a}(t)$ or $ppg_{\lambda_b}(t)$:

$$ppg_{\lambda_b}(t) = \frac{S_{\lambda_a}(t) - r_v \cdot S_{\lambda_b}}{(r_a - r_v)}$$

$$ppg_{\lambda_a}(t) = r_a \cdot ppg_{\lambda_b}(t) = \frac{r_a(S_{\lambda_a}(t) - r_v \cdot S_{\lambda_b})}{(r_a - r_v)}$$

Herein, $ppg_{\lambda_a}(t)$ and $ppg_{\lambda_b}(t)$ both represent the signal with motion interference being eliminated; $r_a$ represents the preset coefficient corresponding to the maximum correlation coefficient, $r_v$ represents the preset coefficient corresponding to the minimum correlation coefficient.

Subsequently, the pulse and other physiological parameters can be accurately calculated by using the signal $ppg_{\lambda_a}(t)$ or $ppg_{\lambda_b}(t)$ with motion interference being eliminated and adopting the time domain waveform algorithm or the frequency domain algorithm, according to needs.

It needs to be noted that, although $ppg_{\lambda_a}(t)$ and $ppg_{\lambda_b}(t)$ are the pulse signals extracted from the first signal and the second signal with different wavelengths, frequencies of the pulse signals (that is, the signals with motion interference being eliminated) $ppg_{\lambda_a}(t)$ and $ppg_{\lambda_b}(t)$ are the same, that is, they have the same wavelengths, thus, the pulse and other physiological parameters calculated according to the pulse signals (that is, the signals with motion interference being eliminated) $ppg_{\lambda_a}(t)$ and $ppg_{\lambda_b}(t)$ are the same.

In this embodiment, dimensionality reduction is performed on the multi-dimensional acceleration signal to obtain a one-dimensional acceleration signal that represents motion interference; the first signal and the second signal are mixed through a plurality of preset coefficients respectively, and a plurality of mixed signals corresponding to the plurality of preset coefficients are calculated; a correlation coefficient between each of the mixed signals and the one-dimensional acceleration signal is calculated accordingly; then a preset coefficient corresponding to the maximum correlation coefficient among the correlation coefficients and a preset coefficient corresponding to the minimum correlation coefficient among the correlation coefficients are obtained; so that a signal with motion interference being eliminated from the measurement signal to be processed is calculated according to the first signal, the second signal, the preset coefficient corresponding to the maximum correlation coefficient, and the preset coefficient corresponding to the minimum correlation coefficient. That is, interference in motion is eliminated by using the correlation between motion interference and the multi-dimensional acceleration signal, and detection of signals with motion interference being eliminated is suitable in various motion states, meanwhile computational complexity is less, and implementation is easily be performed on the wearable device.

A second embodiment of the present disclosure provides a method for eliminating motion interference. This embodiment is a refinement of the first embodiment, and the main refinement lies in: detailed introduction is provided to step 101 of performing dimensionality reduction on the multi-dimensional acceleration signal to obtain a one-dimensional acceleration signal that represents motion interference.

A specific flow of the method for eliminating motion interference in this embodiment is shown in FIG. 2.

Herein, steps 202 to 205 are roughly the same as steps 102 to 105, no more details are repeated here. The main difference lies in: in this embodiment, step 201 of performing dimensionality reduction on the multi-dimensional acceleration signal to obtain a one-dimensional acceleration signal that represents motion interference comprises the following sub-steps in details:

Sub-step 2011, a covariance matrix of a multi-dimensional acceleration matrix formed by the multi-dimensional acceleration signal is calculated.

Specifically, a multi-dimensional acceleration signal usually is a three-axis acceleration signal G(t). The three-axis acceleration signal G(t) indicates the acceleration signals in different directions in a three-dimensional space. The three-dimensional data G(t)=[x(t),y(t),z(t)], x(t),y(t),z(t) indicate the accelerations in three directions, respectively, thus the covariance matrix C of the three-dimensional data G(t) may be calculated as:

$$C = \begin{bmatrix} cov(x,x) & cov(x,y) & cov(x,z) \\ cov(y,x) & cov(y,y) & cov(y,z) \\ cov(z,x) & cov(z,y) & cov(z,z) \end{bmatrix}$$

Herein, cov represents calculating a covariance.

Sub-step 2012, a plurality of eigenvalues and a plurality of eigenvectors of the covariance matrix are calculated.

Specifically, the eigenvalues of the covariance matrix C are $\lambda_i$, and the eigenvectors corresponding to the eigenvalues $\lambda_i$ are $v_i$, herein i=1, 2, 3; thus, the following formula is satisfied:

$$Cv_i = \lambda_i v_i$$

Accordingly, the eigenvalues $\lambda_i$ and the eigenvectors $v_i$ corresponding thereto can be obtained, that is, the plurality of eigenvalues correspond to the plurality of eigenvectors respectively.

Sub-step 2013, an eigenvector that includes a preset information weight is identified from the plurality of eigenvectors according to the plurality of eigenvalues.

Specifically, the plurality of eigenvalues $\lambda_i$ are sorted form maximum to minimum, and sequences of the eigenvectors $v_i$ corresponding to the eigenvalues $\lambda_i$ are adjusted accordingly, the adjusted eigenvalues are represented by $\lambda_I$, and the corresponding eigenvectors are represented by $v_I$; herein I=1, 2, 3.

The preset information weight represents a percentage of each eigenvector in all eigenvectors, expressed as p %;

When $$\frac{\sum_{i=1}^{i=I-1} \lambda_I}{\sum_{i=1}^{i=3} \lambda_I} < p\ \%, \text{ and } \frac{\sum_{i=1}^{i=I} \lambda_I}{\sum_{i=1}^{i=3} \lambda_I} \geq p\ \%,$$

it indicates that the eigenvector $v_I$ corresponding to the eigenvalues $\lambda_I$ includes a preset information weight; herein I=1, 2, 3.

Accordingly, an eigenvector V=[$v_1, \ldots v_I$] that includes a preset information weight can be identified from the plurality of eigenvectors.

Sub-step 2014, the eigenvector is multiplied with the multi-dimensional acceleration signal, so as to obtain the one-dimensional acceleration signal.

Specifically, the eigenvector V that includes a preset information weight is multiplied with the three-axis acceleration signal G(t) (that is, the multi-dimensional acceleration signal), to obtain the dimensionality-reduced three-axis acceleration signal G'(t):

$$G'(t) = G(t)V$$

Herein, G'(t) represents the dimensionality-reduced three-axis acceleration signal.

The dimensionality-reduced three-axis acceleration signal G'(t) is a T*I-dimensional matrix, I=1, 2, 3, and it may be further represented as:

$$G'(t) = [g_1(t), \ldots g_I(t)]$$

Accordingly, the one-dimensional acceleration signal Acc(t) can be obtained, $$Acc(t) = \sum_{i=1}^{i=I} g_i(t)$$

In comparison to the first embodiment, this embodiment provides a specific mode of implementing dimensionality reduction processing on the multi-dimensional acceleration signal.

Figure 5:
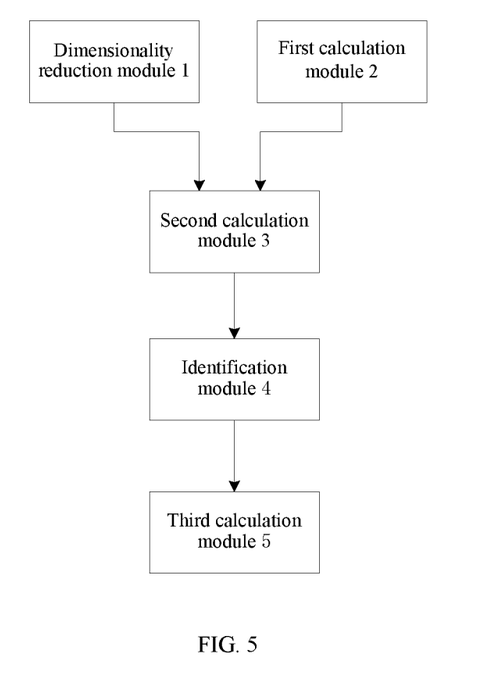
FIG. 5 is a schematic block diagram of an apparatus for eliminating motion interference according to a third embodiment of the present disclosure.

A third embodiment of the present disclosure provides an apparatus for eliminating motion interference, which is applied to the method for eliminating motion interference in any one of the first embodiment and the second embodiment. In this embodiment, as shown in FIG. 5, the apparatus for eliminating motion interference includes a dimensionality reduction module 1, a first calculation module 2, a second calculation module 3, an identification module 4, and a third calculation module 5.

The dimensionality reduction module 1 is configured to perform dimensionality reduction on a multi-dimensional acceleration signal to obtain a one-dimensional acceleration signal that represents motion interference.

The first calculation module 2 is configured to mix a first signal and a second signal through a plurality of preset coefficients respectively, so as to calculate a plurality of mixed signals corresponding to the plurality of preset coefficients.

The second calculation module 3 is configured to calculate a correlation coefficient between each of the mixed signals and the one-dimensional acceleration signal.

The identification module 4 is configured to obtain a preset coefficient corresponding to the maximum correlation coefficient among the correlation coefficients and a preset coefficient corresponding to the minimum correlation coefficient among the correlation coefficients.

The third calculation module 5 is configured to calculate a signal with motion interference being eliminated from the measurement signal to be processed, according to the first signal, the second signal, the preset coefficient corresponding to the maximum correlation coefficient, and the preset coefficient corresponding to the minimum correlation coefficient.

In this embodiment, dimensionality reduction is performed on the multi-dimensional acceleration signal to obtain a one-dimensional acceleration signal that represents motion interference; the first signal and the second signal are mixed through a plurality of preset coefficients respectively, and a plurality of mixed signals corresponding to the plurality of preset coefficients are calculated; a correlation coefficient between each of the mixed signals and the one-dimensional acceleration signal is calculated accordingly; then a preset coefficient corresponding to the maximum correlation coefficient among the correlation coefficients and a preset coefficient corresponding to the minimum correlation coefficient among the correlation coefficients are obtained; so that a signal with motion interference being eliminated from the measurement signal to be processed is calculated according to the first signal, the second signal, the preset coefficient corresponding to the maximum correlation coefficient, and the preset coefficient corresponding to the minimum correlation coefficient. That is, interference in motion is eliminated by using the correlation between motion interference and the multi-dimensional acceleration signal, and detection of signals with motion interference being eliminated is suitable in various motion states, meanwhile computational complexity is less, and implementation is easily be performed on the wearable device.

Figure 6:
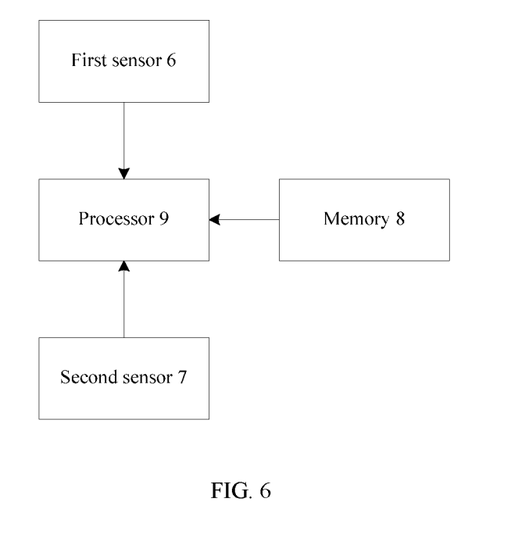
FIG. 6 is a schematic block diagram of a wearable device according to a fourth embodiment of the present disclosure.

A fourth embodiment of the present disclosure provides a wearable device, which is any one of a watch, a ring, a headband and an earphone. In this embodiment, as shown in FIG. 6, the wearable device comprises a first sensor 6, a second sensor 7, a memory 8, and a processor 9.

In this embodiment, the processor 9 is connected to the first sensor 6 and the second sensor 7.

The first sensor 6 is configured to acquire a multi-dimensional acceleration signal of the wearable device.

The second sensor 7 is configured to obtain a measurement signal to be processed; and the measurement signal to be processed includes a first signal and a second signal having different wavelengths. Herein the second sensor 7 may be a heart rate sensor.

The memory 8 is configured to store a plurality of instructions.

The processor 9 is configured to load the plurality of instructions and perform the function of the apparatus for eliminating motion interference in the third embodiment.

This embodiment provides a wearable device capable of eliminating motion interference.

It is understandable to those ordinary skilled in the art that the above embodiments are specific examples in the present disclosure, and in practical applications, various changes can be made in form and in detail without deviating from the spirit and scope of the present disclosure.

What is claimed is:

1. A method for eliminating motion interference, comprising:

acquiring, by a first sensor of a wearable device comprising a first sensor, a second sensor, a memory, and a processor connected to the first sensor and the second sensor, a multi-dimensional acceleration signal of the wearable device;

obtaining, by the second sensor, a measurement signal to be processed, wherein the measurement signal to be processed includes a first signal and a second signal having different wavelengths;

executing, by the processor, a plurality of instructions stored in the memory, to eliminate motion interference, comprising:

performing, by the processor, dimensionality reduction on the multi-dimensional acceleration signal to obtain a one-dimensional acceleration signal that represents motion interference;

mixing, by the processor, the first signal and the second signal through a plurality of preset coefficients respectively, so as to calculate a plurality of mixed signals corresponding to the plurality of preset coefficients;

calculating, by the processor, a correlation coefficient between each of the mixed signals and the one-dimensional acceleration signal;

obtaining, by the processor, a preset coefficient corresponding to the maximum correlation coefficient among the correlation coefficients and a preset coefficient corresponding to the minimum correlation coefficient among the correlation coefficients; and calculating, by the processor, a signal with motion interference being eliminated from the measurement signal to be processed, according to the first signal, the second signal, the preset coefficient corresponding to the maximum correlation coefficient, and the preset coefficient corresponding to the minimum correlation coefficient.

2. The method according to claim 1, wherein the mixed signal $D_{r_i}(t)$ is:

$$D_{r_i}(t) = S_{\lambda_a}(t) - r_i \cdot S_{\lambda_b}, \ i=1, 2, 3, \ldots;$$

$S_{\lambda_a}(t)$ represents the first signal; $S_{\lambda_b}$ represents the second signal; $r_i$ represents an i-th preset coefficient, and a traversal range of $r_i$ is $[r_{slow}, r_{high}]$, wherein $r_{slow}$, $r_{high}$ are a lower limit and an upper limit of the traversal range, respectively.

3. The method according to claim 2, wherein the signal with motion interference being eliminated is expressed as:

$$ppg_{\lambda_a}(t) = \frac{r_a(S_{\lambda_a}(t) - r_v \cdot S_{\lambda_b})}{(r_a - r_v)}, \text{ or } ppg_{\lambda_b}(t) = \frac{S_{\lambda_a}(t) - r_v \cdot S_{\lambda_b}}{(r_a - r_v)};$$

wherein $g_{\lambda_a}(t)=r_a \cdot ppg_{\lambda_a}(t)$, and $ppg_{\lambda_a}(t)$ and $ppg_{\lambda_b}(t)$ both represent the signal with motion interference being eliminated; $r_a$ represents the preset coefficient corresponding to the maximum correlation coefficient, $r_v$ represents the preset coefficient corresponding to the minimum correlation coefficient.

4. The method according to claim 1, wherein the correlation coefficient comprises a Pearson correlation coefficient.

5. The method according to claim 1, wherein performing dimensionality reduction on the multi-dimensional acceleration signal to obtain a one-dimensional acceleration signal that represents motion interference specifically comprises:
calculating a covariance matrix of a multi-dimensional acceleration matrix formed by the multi-dimensional acceleration signal;
calculating a plurality of eigenvalues and a plurality of eigenvectors of the covariance matrix; the plurality of eigenvalues corresponding to the plurality of eigenvectors respectively;
identifying, according to the plurality of eigenvalues, an eigenvector that includes a preset information weight from the plurality of eigenvectors; and
multiplying the eigenvector with the multi-dimensional acceleration signal to obtain the one-dimensional acceleration signal.

6. The method according to claim 1, wherein the value of the plurality of preset coefficients is increased in an arithmetic progression manner.

7. The method according to claim 1, wherein the signal with motion interference being eliminated comprises a PPG signal.

8. An apparatus for eliminating motion interference, which is applied to a wearable device comprising a first sensor, a second sensor, a memory, and a processor connected to the first sensor and the second sensor;
wherein the first sensor is configured to acquire a multi-dimensional acceleration signal of the wearable device;
the second sensor is configured to obtain a measurement signal to be processed; and the measurement signal to be processed includes a first signal and a second signal having different wavelengths;
the memory is configured to store a plurality of instructions; and
the processor is configured to execute the plurality of instructions in the memory, to:
perform dimensionality reduction on the multi-dimensional acceleration signal to obtain a one-dimensional acceleration signal that represents motion interference;
a mix the first signal and the second signal through a plurality of preset coefficients respectively, so as to calculate a plurality of mixed signals corresponding to the plurality of preset coefficients;
a calculate a correlation coefficient between each of the mixed signals and the one-dimensional acceleration signal;
a obtain a preset coefficient corresponding to the maximum correlation coefficient among the correlation coefficients and a preset coefficient corresponding to the minimum correlation coefficient among the correlation coefficients; and
a calculate a signal with motion interference being eliminated from the measurement signal to be processed, according to the first signal, the second signal, the preset coefficient corresponding to the maximum correlation coefficient, and the preset coefficient corresponding to the minimum correlation coefficient.

9. A wearable device comprising a first sensor, a second sensor, a memory, and a processor connected to the first sensor and the second sensor;
wherein the first sensor is configured to acquire a multi-dimensional acceleration signal of the wearable device;
the second sensor is configured to obtain a measurement signal to be processed; and the measurement signal to be processed includes a first signal and a second signal having different wavelengths;
the memory is configured to store a plurality of instructions; and
the processor is configured to execute the plurality of instructions in the memory, to: perform the function of an apparatus for eliminating motion interference
a perform dimensionality reduction on the multi-dimensional acceleration signal to obtain a one-dimensional acceleration signal that represents motion interference;
a mix the first signal and the second signal through a plurality of preset coefficients respectively, so as to calculate a plurality of mixed signals corresponding to the plurality of preset coefficients;
a calculate a correlation coefficient between each of the mixed signals and the one-dimensional acceleration signal;
a obtain a preset coefficient corresponding to the maximum correlation coefficient among the correlation coefficients and a preset coefficient corresponding to the minimum correlation coefficient among the correlation coefficients; and
a calculate a signal with motion interference being eliminated from the measurement signal to be processed, according to the first signal, the second signal, the preset coefficient corresponding to the maximum correlation coefficient, and the preset coefficient corresponding to the minimum correlation coefficient.

10. The wearable device according claim 9, wherein the second sensor comprises a heart rate sensor.

* * * * *